(12) United States Patent
Scarborough et al.

(10) Patent No.: US 10,639,157 B2
(45) Date of Patent: May 5, 2020

(54) DEMINERALIZED BONE FIBER COMPOSITION FOR USE IN MINIMALLY INVASIVE SURGERY

(71) Applicant: THERACELL, INC., Northridge, CA (US)

(72) Inventors: Nelson L. Scarborough, Andover, MA (US); Andrew J. Carter, Stow, MA (US); Bradley E. Patt, Northridge, CA (US)

(73) Assignee: Theracell, Inc., Sherman Oaks, CA (US)

( * ) Notice: Subject to any disclaimer, the term of this patent is extended or adjusted under 35 U.S.C. 154(b) by 100 days.

(21) Appl. No.: 15/921,583

(22) Filed: Mar. 14, 2018

(65) Prior Publication Data

US 2018/0263779 A1    Sep. 20, 2018

Related U.S. Application Data

(60) Provisional application No. 62/471,284, filed on Mar. 14, 2017.

(51) Int. Cl.
*A61F 2/28* (2006.01)
*A61F 2/30* (2006.01)

(52) U.S. Cl.
CPC .............. *A61F 2/2846* (2013.01); *A61F 2/28* (2013.01); *A61F 2002/285* (2013.01); *A61F 2002/2835* (2013.01); *A61F 2002/3096* (2013.01); *A61F 2002/30225* (2013.01); *A61F 2002/30235* (2013.01); *A61F 2002/30588* (2013.01); *A61F 2310/00359* (2013.01)

(58) Field of Classification Search
CPC ... A61F 2/28; A61F 2/2846; A61F 2002/2835
See application file for complete search history.

(56) References Cited

U.S. PATENT DOCUMENTS

| | | | |
|---|---|---|---|
| 4,348,377 | A | 9/1982 | Felder et al. |
| 4,639,366 | A | 1/1987 | Heller |
| 4,764,364 | A | 8/1988 | Heller et al. |
| 4,765,973 | A | 8/1988 | Heller |
| 4,877,864 | A | 10/1989 | Wang et al. |
| 5,013,649 | A | 5/1991 | Wang et al. |
| 5,073,362 | A | 12/1991 | Blaszkiewicz et al. |
| 5,106,748 | A | 4/1992 | Wozney et al. |
| 5,108,922 | A | 4/1992 | Wang et al. |
| 5,116,738 | A | 5/1992 | Wang et al. |
| 5,366,875 | A | 11/1994 | Wozney et al. |
| 5,447,711 | A | 9/1995 | Almen et al. |

(Continued)

FOREIGN PATENT DOCUMENTS

| | | |
|---|---|---|
| EP | 0023992 A1 | 2/1981 |
| EP | 0033426 A2 | 8/1981 |

(Continued)

*Primary Examiner* — Jason-Dennis N Stewart
(74) *Attorney, Agent, or Firm* — Umberg Zipser LLP (57) ABSTRACT

A bone implant composition and methods thereof include bone material made into various implant shapes including a cylinder having an outermost layer and an inner layer completely surrounded by the outermost layer. The bone implant compositions and methods include a bag or cylindrical tube made from a bone material which may be filled with additional bone material.

10 Claims, 5 Drawing Sheets

(56) References Cited

U.S. PATENT DOCUMENTS

| | | | |
|---|---|---|---|
| 5,695,742 | A | 12/1997 | Felder et al. |
| 6,616,698 | B2 | 9/2003 | Scarborough |
| 6,630,153 | B2 | 10/2003 | Long et al. |
| 9,486,557 | B2 | 11/2016 | Carter et al. |
| 9,572,912 | B2 | 2/2017 | Scarborough et al. |
| 2016/0256607 | A1* | 9/2016 | Francis ............... A61L 27/3608 |

FOREIGN PATENT DOCUMENTS

| | | |
|---|---|---|
| EP | 0168277 A1 | 1/1986 |
| EP | 0177414 A1 | 4/1986 |
| EP | 0308364 A2 | 3/1989 |
| WO | WO85/01727 | 4/1985 |
| WO | WO92/08691 | 5/1992 |
| WO | WO93/00432 | 1/1993 |
| WO | WO94/26892 | 11/1994 |
| WO | WO94/26893 | 11/1994 |
| WO | WO2016/123583 A1 | 8/2016 |

* cited by examiner

DEMINERALIZED BONE FIBER COMPOSITION FOR USE IN MINIMALLY INVASIVE SURGERY

CROSS-REFERENCE TO RELATED APPLICATION(S)

The present application claims priority to and the benefit of U.S. Provisional Application Ser. No. 62/471,284 filed on Mar. 14, 2017, entitled "Demineralized Bone Fiber Composition For Use in Minimally Invasive Surgery," the entire content of which is incorporated herein by reference.

BACKGROUND

Bone grafts are commonly used to treat defects in the skeletal system caused by injury or disease. Skeletal defects often require bone grafts to maintain space and provide a matrix for healing. A graft should provide or facilitate the various mechanisms of bone healing including osteoconduction, osteoinduction, and osteogenesis.

Osteoconduction is the ability of the graft to act as a matrix or scaffold to support bone formation. Osteoinduction is a result of bone growth factors that stimulate differentiation of local cells to become bone forming cells, i.e. osteoblasts. Bone morphogenic proteins (BMP's) that are naturally occurring in bone, or that may be produced by recombinant gene technologies, are responsible for osteoinduction. Osteogenesis refers to the formation of bone, and may also be used to reference the ability of cells, to form bone. Bone forming cells may either be resident at the graft site or transplanted to the site by autogenous bone, bone marrow aspirate and/or cell implantation.

As no 'ideal' bone graft currently exists, autograft bone, often recovered from patients' iliac crest, is considered the "gold standard." However, autograft bone involves additional surgical trauma to the patient, time/cost of additional surgical time and supplies, and often results in patient morbidity that may be slow to resolve. Quantities of autograft bone are also limited, and this becomes more problematic in patients with prior bone harvesting procedures. Furthermore, the healing rates, particularly recognized in animal models designed to study bone graft performance, (e.g., rabbit posterolateral spine fusion) have demonstrated less than optimal results, i.e., 70% spine fusion rates. Considering the requirements to form bone, a need exists for a reproducible and cost-effective process of making a bone graft having improved osteoconductive and osteoinductive properties.

SUMMARY

Aspects of embodiments of the present invention include a bone implant made from a bone material in a form of a cylinder, where the cylinder has length from about 1 cm to about 30 cm and a diameter from about 3 mm to about 15 mm, and the bone material selected from demineralized bone fibers (DBF), a mixture of DBF and cancellous bone, mineralized cortical bone, partially demineralized cortical bone, demineralized cortical bone, or a synthetic bone graft substitute. In some embodiments the bone material is demineralized bone fibers from cortical bone. In some embodiments, the cylinder has an outermost layer that is annealed by heating and/or dehydrothermal treatment. The cylinder may include an outermost layer made from a first type of bone material and an inner layer made from a second type of bone material, where the inner layer is surrounded completely by the outermost layer. In some embodiments, the outermost layer includes DBF fibers and the inner layer includes synthetic bone graft substitute, allograft bone chips, xenograft bone chips, and/or demineralized bone matrix (DBM).

Aspects of embodiments of the present invention include a bone implant bag made from a first sheet of bone material and a second sheet of bone material of each sheet having approximately the same size, each sheet having four sides, the first sheet overlaying the second sheet, and three of the four sides of the first sheet being bonded to the second sheet forming a cavity between the first sheet and the second sheet. The bone implant bag made be made from demineralized bone fibers (DBF), a mixture of DBF and cancellous bone, mineralized cortical bone, demineralized cortical bone, partially demineralized cortical bone, partially demineralized bone fibers, or a synthetic bone graft substitute. In some embodiments, the bone implant bag also includes synthetic bone graft substitute, allograft bone chips, xenograft bone chips, DBF, or any form of DBM added into the cavity between the first sheet and the second sheet. In some embodiments, the bone implant bag has a length from about 5 cm to about 11 cm and a width from about 5 cm to about 11 cm.

Aspects of embodiments of the present invention include a method of making a bone implant for minimally invasive surgery (MIS), including compressing a first bone material into a mold to form a sheet of compressed bone material, and rolling the sheet of compressed bone material to form a cylindrical bone implant. In some embodiments, the method of making a bone implant also includes adding a second bone material to the sheet prior to rolling, the second bone material selected from synthetic bone graft substitute, allograft bone chips, xenograft bone chips, and/or demineralized bone matrix (DBM). The rolling may include using a cigarette roller machine, hand rolling around a mandrel, heat sealing, or suturing.

Aspects of embodiments of the present invention include a method of delivering a bone repair composition to a subject by implanting the bone implant bag as disclosed into the subject. In some embodiments, the method includes suturing the cavity of the bone implant bag closed prior to implanting into the subject.

DETAILED DESCRIPTION

With the continued innovation in minimally invasive surgery (MIS) for orthopedic and spine procedures, a need has arisen to be able to efficiently and accurately place bone grafts into defects deep within a patient's body with minimal access through small incisions. Long, small diameter tubes are used to provide a route for surgical instruments to be guided to the targeted site being operated on. This situation makes it difficult to place bone grafts. There are significant challenges with the currently available bone graft options. When one attempts to deliver bone graft (e.g. autograft, Demineralized Bone Matrix (DBM), or stem cell products with bone matrix) through cannulae it may bind within the cannulae making it difficult and frustrating for the surgeon. Inserting the graft into the tube is challenging and when the plunger or push rod or other transporting mechanism is then inserted to advance the graft, the graft may bind within the cannula. This problem occurs with all of the currently available graft materials creating a problem that has not been solved prior to the technology described in this disclosure.

The reason the graft may bind to cannula appears to be due to several problems. One reason appears to be that the space between the rod and inner diameter of the cannulae tubes allows material to lodge between the plunger and cannula wall during the plunging or advancing step causing friction and binding. Another reason appears to be due to a process known as granular mechanics where particulate material when under pressure becomes extremely hard. This property of granular materials is well known and is used in construction where materials such as sand or gravel are sorted to provide relatively uniformity and then behave as a solid mass when placed into sites and loaded.

The difficulty in delivering bone graft through tubes has several consequences. One is that the graft has to be placed in very small quantities sequentially until adequate volume is achieved. The other is that the additional manipulation and time required accomplishing this increases costs and risks of the surgical procedure. Further, having to exert force to advance the graft opens the possibility of pushing mechanism to be over advanced and damage tissue within the site causing patient injury. Embodiments of the present invention overcome this problem using an approach including a lubricious bone fiber composition, a method of making the lubricious bone fiber composition, a device for forming the bone fiber composition, a device for holding or storing the composition, that may optionally be used to facilitate rehydration with bone marrow aspirate or the addition of autograft, and an apparatus for delivering the composition to a subject using minimally invasive surgery (MIS).

Autograft bone from the patient, allograft bone from donors of the same species, and synthetic bone materials are common options. Allogeneic demineralized bone matrix (DBM) has gained popularity as it has good bone healing characteristics and is readily remodeled by host cells. Synthetic materials based on calcium phosphates or sulphates may also be used.

The popularity of DBM-based products is based on the ability to induce bone formation through expression of inherent non-collagenous proteins that stimulate some cell types present at the graft site to differentiate into bone forming cells. This process has been termed "osteoinduction" and is due to the natural presence of bone morphogenic proteins (BMP's) in bone. DBM is produced by grinding the bone into a powder and then treating it with acid to demineralize it. A disadvantage of DBM is in the handling characteristics of the powder and an excipient such as glycerol or polyoxamer is generally needed to improve handling. A further disadvantage of DBM is its lack of x-ray opacity which means that graft placement cannot be confirmed by radiography.

DBM also provides a scaffold for cells to populate and spread throughout in a process known as osteoconduction. Demineralized bone in the form of a fiber, known as DBF™ (Demineralized Bone Fiber), has a physical form that has been shown to optimize and enhance the osteoconductive performance of DBM. In some embodiments of the present invention, a composition and method of manufacture of DBF fibers is as disclosed in U.S. Pat. Nos. 9,486,557 and 9,572,912, the entire contents of both of which are herein incorporated by reference. When DBM or DBF is combined with cells capable of forming bone by osteogenesis these three mechanisms of bone healing may be combined. Additionally, the DBF fibers of U.S. Pat. Nos. 9,486,557 and 9,572,912 are sufficiently long that they do not require excipients to provide satisfactory handling characteristics. Nonetheless, the use of DBF does not address the lack of x-ray opacity.

Research to optimize bone healing has resulted in several advancements including attempts to enhance each of the processes. Recombinant technologies have been used to produce recombinant BMP's to enhance osteoinduction, while cell concentration and transplantation have been used to enhance osteogenesis and various matrices have been developed to enhance osteoconduction.

A further issue with the use of demineralized bone fiber (DBF™) grafting materials is being able to provide the fiber materials in a form that facilitates efficient and facile surgical introduction into the patient. For many procedures it may be preferable that the size of the incision is minimized to reduce the surgical trauma and patient recovery time. This requires that the graft be delivered through relatively long cannulae (about 15 to 30 cm in length) having relatively small diameter (about 3 to 15 mm in diameter). Embodiments of the present invention encompass a means to form graft materials and control the rehydration rate of the graft and the amount of swelling during rehydration as well as provide a means for surgically delivering the graft individually or sequentially through long cannulae of various inner diameters and to produce them using an efficient and controlled process.

As used herein, "bone fiber pellet," "bone fiber implant," "bone implant," "implant," "graft," "DBF pellet," "DBF implant," and like terms refer to a composition of compressed bone fibers for implant into a subject by any surgical means, including minimally invasive methods.

As used herein, "demineralized" bone refers to bone that has been demineralized to 10% calcium content or less.

As used herein, "partially demineralized" bone refers to bone that has more than 10% calcium content and less than 50% calcium content, or has between 10% and 40% calcium content, between 10 and 30% calcium content, or between 10 and 20% calcium content.

As used herein, "mineralized" bone refers to bone having its natural amount of calcium which is approximately between 50 to 70% calcium.

Figure 5:
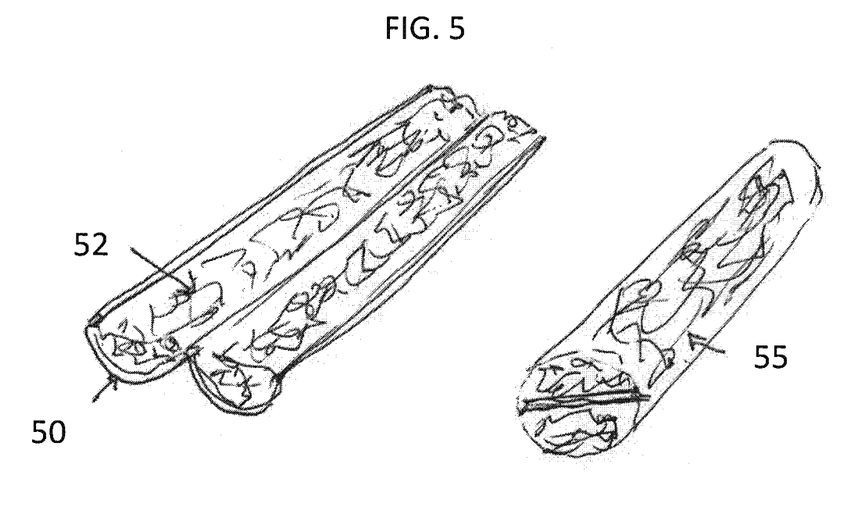
FIG. 5 shows a cylindrical implant, according to embodiments of the present invention. The implant 55 is stored in a flexible mesh carrier 50 as two semi-cylindrical implants 52.
Figure 6:
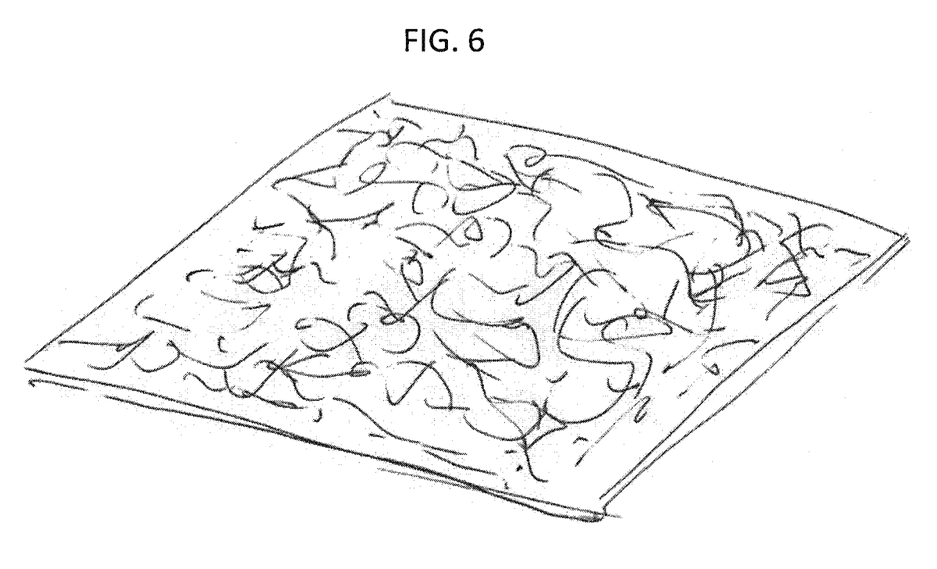
FIG. 6 shows a demineralized bone fiber (DBF) sheet material, according to embodiments of the present invention, the DBF sheet material may be produced using a mold as shown in FIG. 2.
Figure 7A:
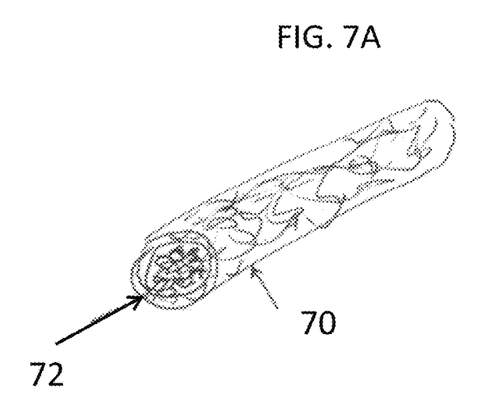
FIG. 7A shows the outer part of the implant 70 is used to hold allogenic bone chips 72 or synthetic graft 72 in place, according to embodiments of the present invention.

As used herein, "annealing", "hardening" and like terms refer to the effect of heating the graft to form intermolecular bonds (i.e., cross-linking) of collagen between collagen molecules. This annealing process may be controlled to occur only at the outermost layer of bone fibers. The outermost layer 50 and 70 are shown in FIGS. 5 and 7A respectively.

As used herein, an "elongated member" is not limited to any particular cross-sectional shape. An example of an elongated member includes a tube, such as a cannula.

The problem of being able to advance the bone graft through narrow tubes has been overcome by developing a graft material such that the issue of granular mechanics is overcome. The bone graft form of the current invention uses bone which has had the mineral component removed by a demineralization process which renders the graft malleable and not hard. The bone is then further formed into fibers by cutting along the long axis such that the collagen fibers within it are maintained in their natural fibrous form, as disclosed in U.S. Pat. Nos. 9,486,557 and 9,572,912, the entire contents of both of which are herein incorporated by reference. This material may then be placed into tubes for delivery.

At this stage, if the demineralized bone fibers (DBF) are pushed through the tube they may be advanced, but the possibility of binding between the tube and rod can still occur due to fibers becoming interposed between the push rod and the inner lumen of the cannula. A further step of the invention is to form the fibers into a cohesive form such that they are coherent and do not have a tendency to become separated and get stuck into this space. The property of the DBFs to form a coherent mass makes them particularly amenable to this application. Fibers are placed into a mold and compressed—either isotropically, uniaxially, horizontally, or vertically. For example, the compression force of the fibers is light or moderate. In one method, fibers are placed into a tube, the opening is covered and the fiber-based graft material is compressed using a plunger. The resulting pre-compacted fiber pellets now take a form analogous to pledgets, i.e. discrete, formed solids that are compressible but do not exhibit granular mechanical properties. This form of graft does not allow for material to become interposed between the rod and tube and thus the graft can be readily advanced without binding. The pellets may be of any diameter suitable for use in MIS surgery. For example, the pellets may be between 3 and 15 mm in diameter, and the length of the pellets may vary from about 1 cm to about 15 cm.

A further refinement and important feature according to embodiments of the present invention, is an additional and optional step in the process where the material is heated. Heating the DBF to between about 40° and 70° C. for a period of 1 min to 300 min to anneal it increases the coherency of the DBF. This increased coherency of the DBF is due to the collagen component undergoing reversible transformation where the triple helix of the collagen molecules unwind slightly, and then when cooled down toward body temperature, (e.g., approximately 37° C.), the intermolecular hydrogen bonds tend to reform to adjacent molecules such that crosslinking occurs. This natural process of forming crosslinking results in the collagen fibers forming a more interconnected architecture.

The other aspect of the heating process of the current invention is that it may be done in a manner that concentrates the crosslinking on the surface of the implant to further maintain the shape of the implant. This surface annealing may be achieved by placing the implant in a heat conductive tube or mold during the heating process. In some embodiments, the heat conductive tube or mold is metallic. In some embodiments, the heat conductive tube or mold is made from stainless steel. The heat conductive nature of the mold provides an annealed outer layer (e.g. a seared outer layer) on the implant, making the implant smooth and lubricious such that advancing through a tube is further facilitated. The heating process may be finely controlled to allow properties to be "dialed in" with great specificity. The surface hardening process may be finely controlled to avoid compromising the porosity of the implant and hence does not interfere with the rehydration of the implant, or with tissue ingrowth while enhancing integrity for placement through a cannula.

An alternative method for maintaining cohesiveness of the graft is to use chemical crosslinking agents such as glutaraldehyde, bis-carbodiimide, water-soluble epoxy crosslinking agents such as 1,4-butanediol diglycidyl ether (BDDGE), diisocyanates, divinyl sulfone (VS), 1,4-butanediol diglycidyl ether (BDDE), ultraviolet radiation, gamma radiation, electron beam radiation, formation of formation of an acyl azides, or other crosslinking agents and methods commonly known in the art. By controlling the process, the crosslinking may be limited to the surface layer of the implant in a manner analogous to the annealing process as described in this disclosure.

A desirable property which has not been previously described or recognized in the art is that in addition to helping hold the shape and adding lubricity, once the graft is placed into the site the surface hardening or annealing maintains the graft in the discrete shape, but if properly done then the graft readily allows rehydration by body fluids and as this occurs allows the graft to swell and fill the void. This property of being able to insert a small graft that then swells and fills the space is of great utility for several reasons. Firstly, it allows for efficient delivery to the site in that a small volume expands to fill a larger volume. Secondly, for bone to form and fill voids it needs a matrix. Bone fills holes poorly without a matrix and this is why grafting is performed. If the graft does not completely fill the defect, voids will remain. Accordingly, fractures must be reduced to close the gap and if this is not done it leads to nonunion and delayed unions. In the case of comminuted fractures that cannot be completely reduced, grafting is required. In MIS procedures, adequate amounts of graft to fill the site and provide complete graft host contact is particularly difficult and risky. If this occurs it is not readily detectable due to limited visualization.

The ability to vary and control the degree of surface hardening by the heating process is a component of the current invention and is important for the improved utility of the graft.

In some embodiments, the methods for making the bone fibers include demineralizing whole bone and subsequently cutting the demineralized bone in a direction parallel to the orientation of collagen fibers within the demineralized bone to form elongated bone fibers. The bone material of the present invention is derived from human (allograft) or animal (xenograft) cortical bone and is processed in such a manner to provide grafts of high utility based on the controlled geometry of the bone fibers. For veterinary applications bone from the same species. i.e. canine for canine patients (allograft) may be used as well as bone from other species (xenograft). It will be obvious to one skilled in the art that fibers other than demineralized bone fibers could be utilized to make a bone graft of this invention. Such fibers could be made from resorbable polymers, or bioactive glasses or mixtures thereof, and could be used in place of, or as an additive to the demineralized bone fibers. The methods of preparation of the graft provide improved efficiency and uniformity with reproducible results and decreased requirements for equipment and resulting costs. The bone graft forms of the present invention do not require the addition of exogenous materials to maintain the form of the graft. These improved characteristics will become apparent to one skilled in the art based upon the present disclosure.

Processing of Fibers.

Processing of the demineralized bone fibers to produce a desired shape or form of the bone fibers may be performed using any suitable method. Examples of bone fiber products for this invention include, but are not limited to: a pellet, bullet, cone, cylinder, tube, and bag. To make some of these forms, the bone fibers may be collected and compressed using pressure molds. In some embodiments, the bone fibers are formed using a wet lay technique as is well understood by those skilled in the art of nonwoven or paper manufacture. Using a wet lay technique, the cut bone fibers are suspended in an aqueous solution to form a bone fiber slurry. Any suitable biocompatible aqueous solution may be used. Non-limiting examples of biocompatible aqueous solutions include: water, saline, and/or solutions including salts such as phosphate buffered saline (PBS), Ringer's solution, Lactated Ringer's solution, and saline with 5% dextrose. In some embodiments of the present invention, cut fibers are placed into saline to create a slurry of entangled bone fibers. The bone fiber slurry is suspended over a mesh screen and the saline is drained resulting in a wet lay process, such that a sheet of demineralized bone fibers is formed on the mesh screen. The thickness of the sheet depends on the amount of fibers and the size of the mesh screen. The resulting fiber sheet may be then dried using heat and/or vacuum or other means such as lyophilization (freeze-drying). In some embodiments, prior to drying, the sheet is placed in a mold and compressed to a defined thickness and shape, followed by drying. Alternatively the sheet may be rolled or wrapped. Following drying the sheet or form derived from the sheet may be cut into pellets. As discussed herein, density, porosity and overall dimensions of the resulting product may be controlled using various molds and techniques.

In some embodiments the screen may itself be contoured to provide a three dimensional shape to the screen such that pellets may be directly produced.

Figure 4:
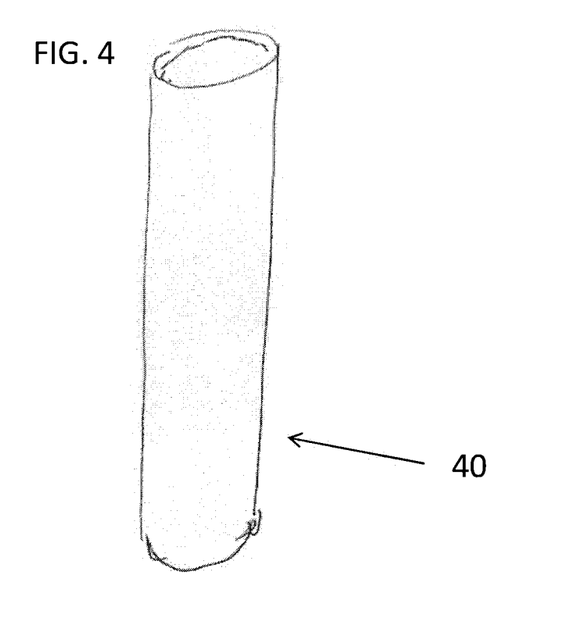
FIG. 4 shows a mold suitable for use to make a cylindrical implant, according to embodiments of the present invention, in which the mold base 40 is a mesh. Optionally, a funnel may be used to facilitate introduction of the DBF fibers into the mold.

Fibers may also be placed into a cylindrical mold cavity and compressed using a plunger or push rod such as is shown in FIG. 4.

In some embodiments, the formed wet lay fiber forms may be placed into an oven and heated as a means to enhance cohesiveness of the bone fiber product. As used herein, "cohesive" and "cohesiveness" are used to refer to the integrity of the bone fiber products. That is, a cohesive bone fiber product stays together, does not fall apart and maintains its shape. As the bone fibers are in a hydrated state, heating to temperatures of about 30° to about 70° C., or about 45 to about 55° C. for about 1 minute up to about 3 hours increases the cohesiveness by increasing the adherence of the collagen to other strands, i.e. annealing or hardening.

In some embodiments a vacuum oven is used whereby the application of vacuum removes moisture and dries the implant. In some embodiments, the process of heating and applying a vacuum includes dehydrothermal treatment as described in Scarborough, U.S. Pat. No. 6,616,698, the entire content of which is herein incorporated by reference.

In some embodiments the heating step is undertaken by placing the implant in contact with a metal or other high heat-conductivity surface such that the degree of annealing/crosslinking is enhanced at that surface.

In some embodiments the implant has a domed or tapered end, or is pellet shape to facilitate subsequent introduction into the delivery system. Shaping the pellet so that the front tip is convex and rear end concave may be beneficial. This may be accomplished by shaping the holder cover, push rod and interfaces accordingly.

In other embodiments, the bone fibers are further processed in a second drying step that may include vacuum drying and/or lyophilization.

In other embodiments the bone fibers may retain some moisture and will be placed in moisture impervious packaging.

In some embodiments the amount of compression, heating, and drying may be tailored to modify the rehydration and re-expansion rates. For example, without heating, the rehydration is fast whereas heating at 55° C. for approximately one hour results in slow re-hydration and re-expansion. By altering these processes, bone fiber compositions as disclosed herein may retain their manufactured shape during packaging, shipment, unpacking and placement into the graft site, but after placement into the graft site, the DBF will begin to absorb moisture rapidly (within about 30 seconds or less) and to be completely re-hydrated/re-expanded within approximately 2 minutes or less. In some embodiments, the DBF composition according to embodiments of the present invention may be completely re-hydrated/re-expanded within 30 seconds.

The ability of the parameters of various stages of the above process to be modified allow for a broad range of products to be produced. A non-limiting range of bone fiber products includes cylinders, pellets, and cones, all of which may be used to fill voids wherever bone formation is required. Example indications that may utilize such an implant product include spine, trauma, dental, craniofacial, and oral maxillofacial surgery.

In some embodiments, bone fiber pellets are formed by adding wet fibers directly into a cylindrical mold. An example of a cylindrical mold is a metal tube as is shown in FIG. 4. A bone fiber pellet shape is useful as it may be delivered to a graft site using a cannula as commonly used for minimally invasive surgery. The bone fiber pellets are capable of passing through a tube. A cylindrical mold is loaded with the fiber. A tamp is used to apply some compression to the fibers. In some embodiments, a fiber loaded cylindrical mold is dried by heat, vacuum, and/or lyophilization. After drying, the bone fiber implant becomes more cohesive and shrinks to a reduced volume. After drying, the bone fiber pellets may be easily expelled out of the mold due to the shrinkage that occurs upon drying. The bone fiber pellets may be subsequently introduced into a liquid, such as water, saline, blood, and/or bone marrow aspirate, and they are readily rehydrated and expanded. After placement into surgical sites, rehydration occurs naturally due to the resident blood and moisture within the site. In some embodiments, one or more such bone fiber pellets may be utilized for minimally invasive grafting procedures such as spinal fusion, trauma and bone cysts as examples.

While wet lay techniques may be used for the manufacture of different shapes from the bone fibers, it will be recognized that any other molding or forming technique used with textile fibers could be used. Fibers with and without excipients may be directly molded using compression into any shape. In some embodiments excipients may be selected that enhance the lubricity of the implant facilitating delivery and further reducing and friction or binding during this procedure.

Long cylindrical implants may not be easily produced using a conventional wet lay process. As an alternative method, implants may be wet laid into a mold with two conjoined semi cylindrical depressions 30 as depicted in FIG. 3.

With reference to FIG. 5, the implants 52 may be stored in this manner in a flexible storage tray 50 and at the time of surgery may be folded together to produce a cylindrical implant 55. The surgeon may also optionally introduce autograft at the time of surgery.

Figure 3:
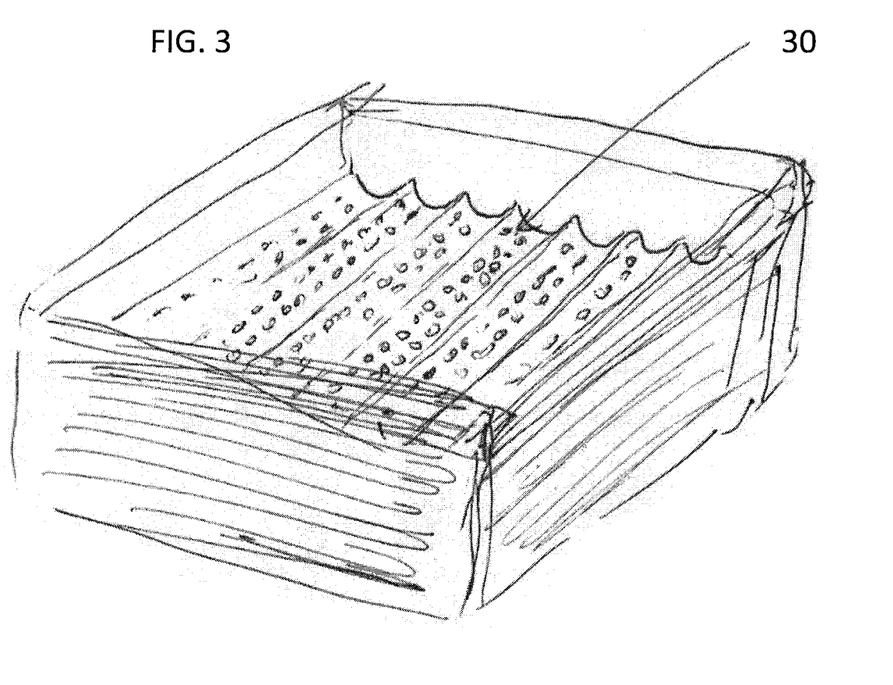
FIG. 3 shows a mold base suitable for use to make a sheet of bone fibers using a wet lay apparatus, according to embodiments of the present invention in which the mesh 30 is provided to allow the fluid to drain through and provide a number of semi-cylindrical implants.

Alternatively, with reference to FIG. 3, semi cylinder implants produced in a mold may be folded together post wet lay and prior to the heat treatment step. At this time the two halves of the cylinder will become entangled and bonded to each other.

Alternatively, multiple rectangular prisms may be wet laid with minimal compression applied and then transferred into a second mold where the lower part of the mold and the lid both have semi cylindrical contours.

Figure 7B:
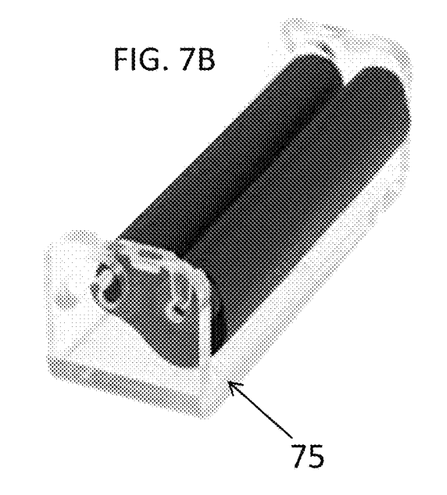
FIG. 7B shows "cigarette" style implants made according to embodiments of the present invention in which a fiber sheet, such as the DBF sheet shown in FIG. 6, is processed to form a cylinder by hand, or using a custom cigarette rolling machine (75).
Figure 7C:
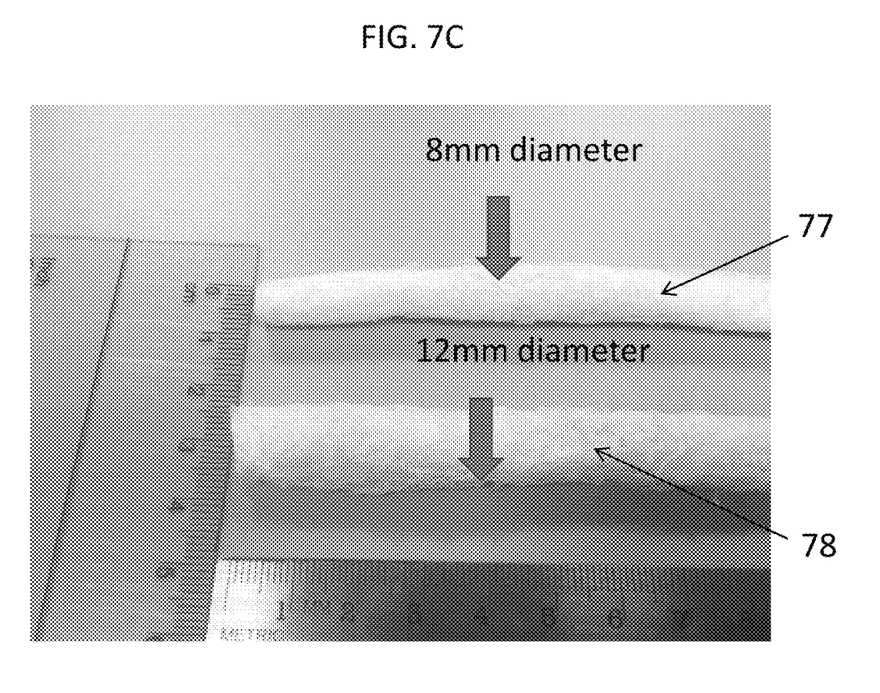
FIG. 7C DBF implants 77 and 78 were made using the rolling machine 75 implants, according to embodiments of the present invention.
Figure 8:
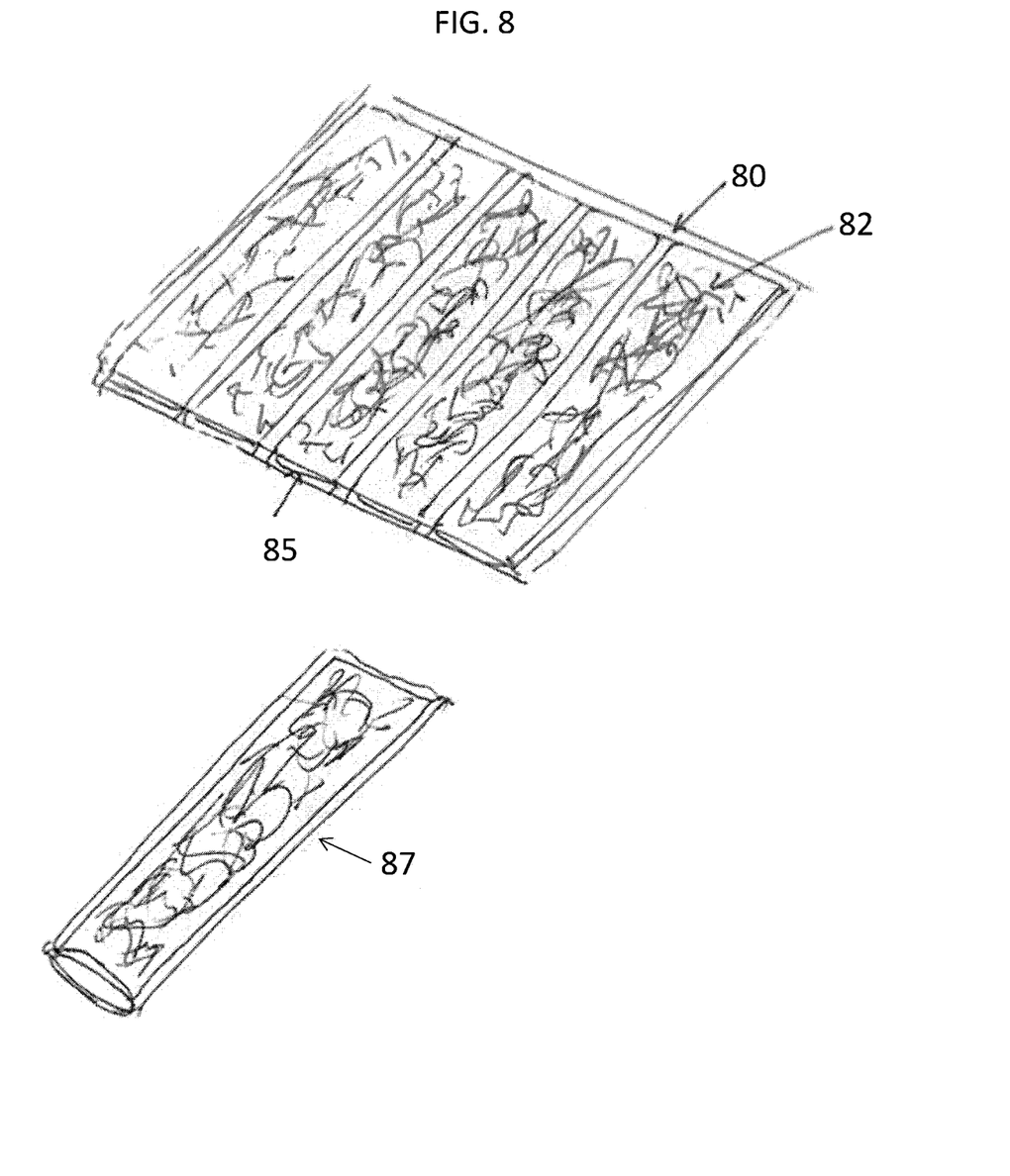
FIG. 8 shows a "graft bag" implant format depicting the areas of densified and bonded fiber 80, the fiber 82, and the opening provided between the two bonded demineralized bone sheets 85, where an individual implant 87 as shown is cut from a larger demineralized bone sheet, according to embodiments of the present invention.

Entanglement of the fibers may be increased by placing fibers between rollers and rolling, such as may be achieved using a cigarette roller 75. Equipment using the same design as a cigarette roller may be used to produce implants of this invention. The cigarette rolling method allows excellent control of length, diameter and density. For a single level posterior lateral fusion (PLF) procedure an implant approximately 5 cm long may be required to span the space between the two levels. For multiple level procedures implants from 10 to 15 cm may be used, or multiple smaller implants. Example implants 77 and 78 are shown in FIG. 7C.

Alternatively a simple mesh mold may be used to produce an approximate cylindrical implant, whereby the DBF cylinder is the hand rolled to form a cylindrical implant, for example implants 77 and 78.

Figure 2:
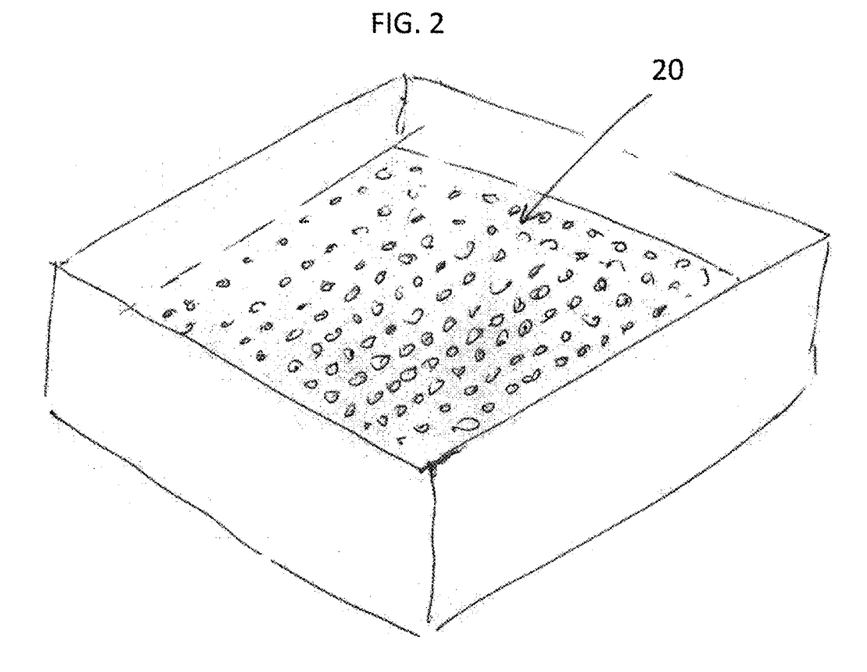
FIG. 2 shows a mold base suitable for use to make a sheet of bone fibers using a wet lay apparatus, according to embodiments of the present invention, in which the mesh 20 is provided to allow the fluid to drain through and provide a uniform flat shape to the sheet.

Sheets of DBF fibers produced through a wet lay process that are between approximately 0.5 mm and 3 mm thick may be produced using a mold as shown in FIG. 2. The holes, or mesh base of the mold 20 allow the fluid component of the fiber slurry to pass, through trapping the fibers onto the flat surface of the screen. The sheets may then be rolled into cylinders by hand or by the cigarette roller technique. These cylinders may have a relatively uniform density of DBF fibers or a "filler" of synthetic bone graft substitute, allograft bone chips, xenograft bone chips, DBF, DBM or other can be introduced as the "tobacco" part of the cigarette. The bone chips may be mineralized, or partially or fully demineralized. Thus, as shown in FIG. 7A, an implant comprises an outer DBF fiber portion 70 enclosing a second graft composition ("filler") 72 as the inner layer completely surrounded by the outermost DBF layer 70.

In an alternative embodiment a removable mandrel may be used in the cigarette roller 75, or hand rolling process such that the implant formed is an empty tube that is designed to be filled by the surgeon at the time of surgery. Optionally one end of the tube may be closed, either by crimping it prior to the heat treatment step, or by sewing it closed using resorbable suture. The mandrel, if made of metal, facilitates heat transfer during the heating step. The mandrel may be oval or of other cross section as desired. Implants with an oval cross section may provide better implant contact with the transverse processes in a posterior lateral fusion application.

In an alternative method of graft containment, thin DBF sheets may be formed into bags by sealing two sheets together on three of the four sides leaving the fourth side open to receive bone grafting materials of any sort—autologous or allogenic bone chips, synthetic bone chips, DBF or DBM. The bag allows ease of introduction and graft containment at the grafting site. The DBF sheets are formed by wet laying in a plain mold. Two sheets are placed together (overlaid) with a siliconized paper sheet or similar placed in the areas where bonding of the two sheets is not required. The sheets are placed in a second mold in which the areas to be bonded are compressed. The mold is then placed into an oven set at 40° to 60° C. for about 1 hour. After cooling the bag may be removed from the mold and the siliconized paper sheet removed. DBF bags my be made from sheets that are approximately 5 cm to 11 cm in length by 5 cm to 11 cm in width with a thickness between 0.5 to 3 mm. Some DBF sheets are about 10 cm by about 11 cm and are approximately 1 to 2 mm thick. The resulting DBF bag has the same width and length as the DBF sheet and is thicker than each DBF sheet depending on the bonding and the optional addition of bone graft materials.

Areas where bonding is required may optionally be needled using barbed needles, as is used in the textile industry to entangle non wovens.

Alternatively, areas where bonding is required may be sewn or sutured using a suture material. In some embodiments, the suture material is bioresorbable and/or radiopaque.

In some embodiments, the graft bags may have any suitable dimensions. For example, the graft bags may be approximately 5 cm to approximately 10 cm long and approximately 1.5 cm wide with an opening on the shorter side for use in posterolateral fusion, and introduction down a MIS tube. Bags for use in interbody fusion may be up to 3 cm wide by 3 cm long. Openings in the bags may optionally be sutured closed prior to implantation.

Alternatively, entanglement may be increased by stirring the fibers while in a liquid slurry. By creating a vortex fibers are swirled and induced to become entangled. This results in non-woven 'ropes' of fibers that can then be cut to length and used as is, or further processed into pellets as described within this disclosure.

Where it is required that the implants are able to swell post implantation so that they are substantially space-filling this is achieved by careful control of the processing conditions such as the optional compression of the fibers and the optional heating and optional drying steps.

Excipients and Additives.

The ability of the demineralized bone fiber products to mix with autograft bone, bone marrow aspirate and other materials improves the surgical utility of an implant made from the demineralized bone fibers of the present invention. Various aspects of product design including density, porosity, etc. influence the mixability and handling and may be incorporated into the design to maximize these properties. The ability to control the geometry of the demineralized bone fiber particles allows for tailoring the product for the indication.

In some embodiments of the present invention, incorporation of excipients may enhance handling properties of the bone graft and or ease of manipulation through the elongated member (e.g., tube or cannula). An excipient may be added to the bone material subsequent to demineralization. That is, an excipient may be added to the bone material before, after or concurrently with the bone cutting. Non-limiting examples of excipients that are also referred to as swelling agents, include liquid polyhydroxy compounds and liquid polyhydroxy compound derivatives. The polyhydroxy compounds and derivatives of this type include those which in the pure or concentrated state and at ambient temperature are normally solid or semi-solid but are soluble in a suitable solvent, e.g., water, physiological saline, ethanol, glycerol, glucose, propylene glycol, polyethylene glycol of from 200-1000 molecular weight, etc., or mixtures thereof, to provide a liquid composition.

In particular, useful polyhydroxy swelling agents possess from 2 to about 18 carbons and include such classes of compounds as the acyclic polyhydric alcohols, non-reducing sugars, sugar alcohols, sugar acids, monosaccharides, disaccharides, water-soluble or water dispersible oligosaccharides, polysaccharides and known derivatives thereof. Specific polyhydroxy compounds include ethylene glycol, diethylene glycol, triethylene glycol, 1,2-propanediol, trimethylolethane, trimethylopropane, erythritol, pentaerythritol, polyalkylene glycols such as the polyethylene glycols, xylitol, sorbitol, mannitol, dulcitol, arabinose, xylose, ribose, adonitol, arabitol, rhamose, inositol, fructose, galactose, glucose, mannose, sorbose, sucrose, maltose, lactose, maltitol, lactitol, stachyose, maltopentaose, cyclomaltohexaose, trehalose, carrageenan, agar, alginic acid, guar gum, gum tragacanth, locust bean gum, gum arabic, xanthan gum, amylose, mixtures and copolymers thereof.

Derivatives of the polyhydroxy compounds, in particular, ester derivatives thereof, are also useful as swelling agents. For example, liquid and solid monoesters and diesters of glycerol can be used to good effect, the solid esters being dissolved up to the limit of their solubility in a suitable vehicle, e.g., propylene glycol, glycerol, polyethylene glycol of 200-1000 molecular weight. Liquid glycerol esters include monacetin and diacetin and solid glycerol esters include such fatty acid monoesters of glycerol as glycerol monolaurate, glyceryl monopalmitate, glyceryl monostearate, etc. An example of a carrier herein comprises glyceryl monolaurate dissolved in glycerol or a 4:1 to 1:4 mixture of glycerol and propylene glycol.

In some embodiments, polyhydroxy excipients include glycerol and its liquid monoesters and diesters, e.g., monacetin and diacetin, fructose, trehalose, glucose and sucrose, and mixtures thereof. Where the polyhydroxy compound is a solid, e.g., sucrose, a solvent such as water, glycerol, polyethylene glycol of from 200-1000 average molecular weight, or mixture thereof is used to provide a flowable solution or bone fiber putty.

Additional non-limiting examples of suitable excipients include: lecithin, polyoxamer, hyaluronic acid, alginate, derivatized hyaluronic acids, and modified celluloses including carboxyl methyl cellulose and hydroxypropyl cellulose.

In some embodiments excipients are selected that enhance the lubricity of the implant and facilitate delivery through cannulae by reducing friction. Excipients such as biocompatible fats and oils, surfactants, etc. are particularly amenable to this functionality.

In some embodiments, a biocompatible material (an additive) is included to enhance the osteogenic properties of the bone implant. In some embodiments of the present invention, the bone fiber composition may also include an additive selected from bone marrow cells, mesenchymal stem cells, oxygenating materials (i.e., oxygen carrying materials), oxygen generating compounds, growth factors, antibiotics, antineoplastic agents, or combinations thereof. In some embodiments, the bone repair composition includes oxygenating materials such as a perfluorocarbon (PFC). In some embodiments, the repair composition includes oxygen generating compounds such as peroxides (e.g., hydrogen peroxide, calcium peroxide), perchlorates (e.g., sodium perchlorate, potassium perchlorate) percarbonates (e.g., sodium percarbonate), or perborates (e.g., sodium perborate).

The addition and selection of at least one biocompatible material may depend on the size of the bone graft site and the location of the site. Additional examples of biocompatible materials include: collagen and insoluble collagen derivatives, hydroxyapatite, tricalcium phosphate, and soluble solids and/or liquids dissolved therein, e.g., antiviricides, particularly those effective against HIV and hepatitis; antimicrobials and/or antibiotics such as erythromycin, bacitracin, neomycin, penicillin, polymyxin B, tetracyclines, viomycin, chloromycetin and streptomycins, cefazolin, ampicillin, azactam, tobramycin, clindamycin and gentamycin; amino acids, magainins, peptides, vitamins, inorganic elements, co-factors for protein synthesis; hormones; endocrine tissue or tissue fragments; synthesizers; enzymes such as collagenase, peptidases, and oxidases; polymer cell scaffolds with parenchymal cells; surface cell antigen eliminators; angiogenic drugs and polymeric carriers containing such drugs; collagen lattices; biocompatible surface active agents; antigenic agents; cytoskeletal agents; cartilage fragments, living cells such as chondrocytes, bone marrow cells, mesenchymal stem cells, natural extracts, tissue transplants, bioadhesives, bone morphogenic proteins (BMPs), transforming growth factor (TGF-beta), insulin-like growth factor (IGF-1); growth hormones such as somatotropin; bone digestors; antitumor agents; fibronectin; cellular attractants and attachment agents; immuno-suppressants; permeation enhancers, e.g., fatty acid esters such as laureate, myristate and stearate monoesters of polyethylene glycol, enamine derivatives, alpha-keto aldehydes, etc.; nucleic acids; and, bioerodable polymers such as those disclosed in U.S. Pat. Nos. 4,764,364 and 4,765,973 and European Patent Application 168,277. The amounts of such optionally added substances can vary widely with optimum levels being readily determined in a specific case by routine experimentation.

Optionally, the DBF may be mixed with particulate materials. Suitable particulate materials include cancellous bone chips, cortical bone chips, synthetic ceramics such as calcium phosphate, tri-calcium phosphate, hydroxyapaptite, or mixtures thereof. Suitable particle sizes range from 100 micron to 3 mm or greater, depending on application, size of defect being filled, etc. Particulates tend to coat and adhere to the DBF particularly if they are fine powder (e.g., less than 500 micron diameter) or if they have rough surfaces, (e.g., for larger particles in the 500 micron to 3 mm diameter range), as is the case with bone and ceramics prepared as porous materials. Bone materials may be mineralized, partially mineralized, or demineralized.

Addition of particulate additives has potential advantages of adding radiopacity.

Other additives are contemplated to modify biological or other properties of the present invention. Non-limiting examples include growth factors such as bone morphogenetic proteins (BMPs), including BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, and BMP-18; Vascular Endothelial Growth Factors (VEGFs), including VEGF-A, VEGF-B, VEGF-C, VEGF-D and VEGF-E; Connective Tissue Growth Factors (CTGFs), including CTGF-1, CTGF-2, and CTGF-3; Osteoprotegerin, Transforming Growth Factor betas (TGF-.beta.s), including TGF-.beta.-1, TGF-.beta.-2, and TGF-.beta.-3, and inhibitors for tumor necrosis factor (e.g., anti-TNF.alpha.). Morphogens may also include Platelet Derived Growth Factors (PDGFs), including PDGF-A, PDGF-B, PDGF-C, PDGF-D, and GDF-5; rhGDF-5; and LIM mineralization protein, insulin-related growth factor-I (IGF-I), insulin-related growth factor-II (IGF-II), fibroblast growth factor (FGF) and beta-2-microglobulin (BDGF II), as disclosed in the U.S. Pat. No. 6,630,153, the entire contents of which is incorporated herein by reference. The polynucleotides encoding the same may also be administered as gene therapy agents. The preferred bioactive substances are the recombinant human bone morphogenetic proteins (rhBMPs) because they are available in relatively unlimited supply and do not transmit infectious diseases. In some embodiments, the bone morphogenetic protein is a rhBMP-2, rhBMP-4, rhBMP-7, or heterodimers thereof. BMPs are available from Wyeth, Madison, N.J., and may also be prepared by one skilled in the art as described in U.S. Pat. No. 5,366,875 to Wozney et al.; U.S. Pat. No. 4,877,864 to Wang et al.; U.S. Pat. No. 5,108,922 to Wang et al.; U.S. Pat. No. 5,116,738 to Wang et al.; U.S. Pat. No. 5,013,649 to Wang et al.; U.S. Pat. No. 5,106,748 to Wozney et al.; and PCT Patent Nos. WO93/00432 to Wozney et al.; WO94/26893 to Celeste et al.; and WO94/26892 to Celeste et al., the entire contents of all of which are herein incorporated by reference.

In some embodiments of this invention additives that improve the x-ray opacity of the implant may be utilized. Suitable conventional water soluble non-ionic X-ray contrast agents are iodinated aromatic compounds, which have one or several aromatic nuclei that are at least triiodo-substituted. Such agents are shown in U.S. Pat. No. 5,695,742 and comprise CAS (Chemical Abstract Service) registration numbers 31112-62-6 (metrizamide), 60166-93-0 (iopamidol), 78649-41-9 (iomeprol), 73334-07-3 (iopromide), 877771-40-2 (ioversol), 66108-95-0 (iohexol), 89797-00-2 (iopentol), 107793-72-6 (ioxilan), 99139-49-8 (II-1), 75751-89-2 (iogulamide), 63941-73-1 (ioglucol), 63941-74-2 (ioglucamide), 56562-79-9 (ioglunide), 76984-84-0 (MP-7011), 64965-50-0 (MP-7012), 77111-65-0 (MP-10007), 79944-49-3 (VA-7-88), 79944-51-7 (also shown in EP 033426), 79211-10-2 (iosimide), 79211-34-0 (iocibidol), 103876-29-5 (also shown in EP 0177414), 141660-63-1 (iofratol), 92339-11-2 (iodixanol), 79770-24-4 (iotrol), 71767-13-0 (iotasul), 81045-33-2 (iodecol), 143200-04-8 (also shown in WO 92/086), 143199-77-3 (also shown in WO 92/08691), 143200-00-4 (also shown in WO 92/08691), 78341-84-1 (also shown in U.S. Pat. No. 4,348,377), 122731-47-9 (also shown in EP 0308364), 122731-49-1 (also shown in EP 0308364), 99139-65-8 (also shown in WO 85/01727), 99139-62-5 (also shown in WO 85/01727), and 78341-84-1 (also shown in EP 0023992).

Other such water soluble non-ionic X-ray contrast agents are shown in U.S. Pat. No. 5,447,711 and comprise iotrolan, ioxaglate, iodecimol, and iosarcol. Other suitable contrast agents are iotusal, ioxilane, and iofrotal.

Preferably, the water soluble non-ionic X-ray contrast agent has a low osmomolality such as iohexol, iodixanol, ioversol, iopamidol, and iotrolane.

For example, iohexol ($C_{19}H_{26}I_3N_3O_9$) as well as its dimer iodixanol can with advantage be used as a water soluble non-ionic X-ray contrast agent. These substances do not influence bone formation and they have a good biocompatibility in bone.

Alternatively x-ray opacity of the implant may be achieved by addition of Barium Sulphate or some other non-water soluble contrast agent.

In other embodiments of the current invention x-ray opacity is achieved by incorporating non-demineralized or partially demineralized bone wherein the mineral components are naturally radiopaque. Synthetic materials such as hydroxyapatite, tricalcium phosphate, or similar materials may be incorporated into the graft.

Figure 1:
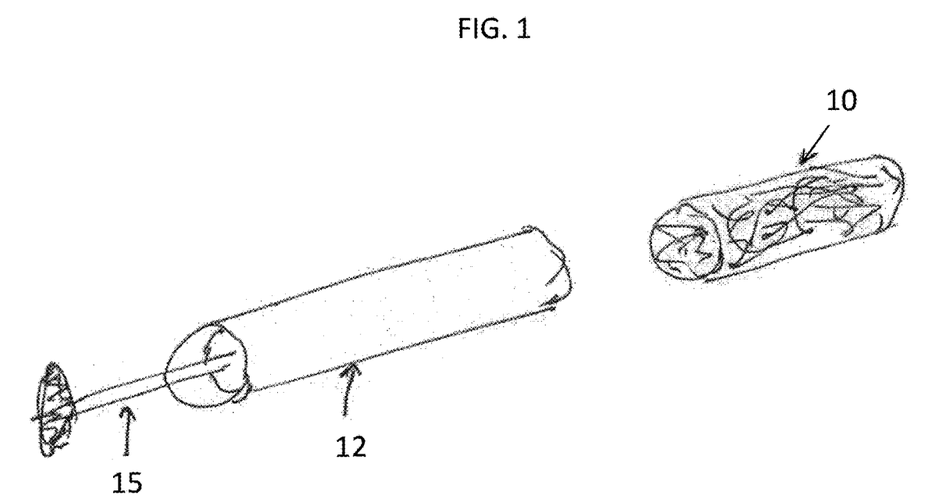
FIG. 1 shows an implant and delivery device, according to embodiments of the present invention, where the implant 10 is placed in the tubular portion of the delivery instrument 12 and is expelled from the device using the plunger 15.

Introduction of an implant of this invention into a patient is accomplished by placing the implant into the proximal end of an elongated member as shown in FIG. 1. The elongated member 12 is placed into the patient through a minimal incision and the distal end of the tube is placed at the point where delivery of the implant 15 is required. This may be confirmed by means of fluoroscopic imaging or other means. When the surgeon is satisfied that the positioning is correct the implant may be advanced down the tube and out into the patient by means of a plunger 15.

The delivery tube may be straight or curved. In the latter instance the plunger will be flexible, being made of nitinol wire or braided nitinol wire or other suitable material.

In some embodiments the implant will be sized exactly to the required implant size, for example, to fit into the cavity in an interbody fusion cage. Alternatively, the required implant volume will require a number of discrete 'pellets' to facilitate delivery, or to allow for placement of graft at multiple locations within the surgical site.

The DBF pellet may be shaped with a convex proximal end and concave distal end by the push rod. Alternatively implants can be introduced by separate means into the end of the delivery tube. Implants having a pellet shape are easier to introduce into delivery tubes.

In some embodiments implants are formed and stored in tubes. To facilitate loading into the end of the delivery tube a recess is formed in the end of the elongated member (e.g., cannula) to hold the storage tube in correct alignment.

In some embodiments a plurality of implants are stored in a holder that is configured to attach to a delivery tube to allow easy deployment of implants.

At the time of surgery, prior to implantation, a small amount of a water soluble contrast agent such as Iopamidol may be injected into the implant to provide visualization during implantation.

EXAMPLES

The following examples use cortical bovine (cow) bone. As discussed herein, either human or animal bone may be used as a source of cortical bone. Fibers were produced using the methodology described in U.S. Pat. Nos. 9,486,557, 9,572,912 and WO 2016/123583, the entire contents of all of which are herein incorporated by reference.

Example 1

FIG. 7C illustrates Cylindrical DBF implants 77 and 78 which were formed using a mesh screen formed into an 'L' shape and then submerged in a tray containing PBS. In a beaker, 2 grams of blotted DBF was added to 25 mls PBS and stirred to create a slurry. The slurry was then applied to the screen submersed in PBS in the tray. The slurry was manipulated with a spatula to evenly distribute the fibers along the width of the screen and align the fibers lengthwise in the screen trough. By performing this step with submersed fibers they are more readily manipulated and also more effectively entangled to form a cohesive mass. The screen was removed from the trough and use to roll the fibers into a tube and squeeze out some moisture. The fibers were then transferred to an absorbent, non-particulating wipe and rolled manually to compress and remove additional moisture. DBF cylinders were then placed uncovered into a convection oven and heated at 55° C. for about 1 hour or vacuum dried overnight at 27° C. The dried cylinders were then cut into sections of varying lengths ranging from 0.5 cm to 10 cm. A section of each version of the cylinders was placed into PBS and hydration observed. The vacuum dried sample was rehydrated by 1 minute while the heated sample required about 1.5 minutes. The vacuum dried version also appeared to expand more than the heated version.

Example 2

2 mm thick sheets of DBF measuring 10 cm×11 cm were produced using a wet-lay approach. DBF sheets were then cut into 20 to 24 mm wide pieces of 5 cm length. The pieces were then rolled around a mandrel and placed into 8 mm diameter tubes that open lengthwise. The lid was closed and the DBF dried. When the 'boat' was subsequently deployed mimicking placement into the graft site it unrolled and opened to form a flat sheet.

Example 3

A mold as shown in FIG. 3 was used to produce implants as two semi cylindrical halves. A slurry containing 50 grams of DBF fibers suspended in PBS was wet laid. A plain lid was placed on the mold and the mold was then placed in a convection oven set at 55° C. for 1 hour. After cooling for 30 minutes the implants were removed.

Example 4

A mold was made as described in Example 3 except equal weights of cancellous bone chips and DBF mixed in the slurry prior to making the implants. The bone chips adhered to the DBF and were thus evenly distributed throughout the implant.

Example 5

A mold was made as described in Example 4 except porous β tricalcium phosphate (cam Bioceramics) measuring 1 to 3 mm was used in place of the cancellous bone chips.

Example 6

A 10 cm×11 cm by 1 mm thick DBF sheet was produced using 15 grams of DBF. A custom cigarette roller was used to roll the sheet into a cigar shape. The implant was placed in a convection oven at 55° C. for one hour.

Example 7

A 10 cm×4 cm by 1 mm thick DBF sheet was produced. A custom cigarette roller was used to roll the sheet into a cigar shape approximately 8 mm diameter with cortical bone chips placed inside the DBF tube. The implant was placed in a convection oven at 55° C. for one hour.

Example 8

Two 10 cm×11 cm by 0.5 mm thick DBF sheets were produced each from 10 grams of DBF fiber. Four siliconized paper sheets 2 cm×10 cm were placed between the sheets allowing margins for heat sealing. A template the shape of the desired seals was placed on top of the sheet and the mold lid closed, applying pressure on the seal areas. The mold was placed in a convection oven set at 55° C. for one hour. After cooling for 30 minutes the DBF bags were removed, separated from each other by cutting and the siliconized paper removed.

While the present invention has been illustrated and described with reference to certain exemplary embodiments, those of ordinary skill in the art will understand that various modifications and changes may be made to the described embodiments without departing from the spirit and scope of the present invention, as defined in the following claims. Additionally, although relative terms such as "outer," "inner," "upper," "lower," "below," "above," "vertical," "horizontal" and similar terms have been used herein to describe a spatial relationship of one element to another, it is understood that these terms are intended to encompass different orientations of the various elements and components of the device in addition to the orientation depicted in the figures.

What is claimed is:

1. A method of making a bone implant from a sheet of demineralized bone fibers (DBF) comprising a plurality of elongated bone fibers cut from demineralized bone in a direction parallel to the orientation of collagen fibers, the method comprising:
providing the DBF into a sheet mold to form a sheet of DBF; and
processing the sheet of DBF by:
i) rolling the sheet of DBF to form a cylindrical bone implant or a hollow tube bone implant; or
ii) bonding a first sheet of DBF with a second sheet DBF to form a bone implant bag,
wherein the hollow tube bone implant or the cylindrical bone implant has a length of from about 1 cm to about 30 cm and a diameter of from about 3 mm to about 15 mm.

2. The method of claim 1, further comprising adding a second bone material to the sheet of DBF prior to rolling the sheet of DBF, the second bone material selected from synthetic bone graft substitute, allograft bone chips, xenograft bone chips, and/or demineralized bone matrix (DBM).

3. The method of claim 1, wherein rolling the sheet of DBF to form a cylindrical bone implant comprises using a cigarette roller technique.

4. The method of claim 1, wherein rolling the sheet of DBF to form a hollow tube bone implant comprises hand rolling the sheet around a mandrel.

5. The method claim 4, wherein the mandrel has an oval cross section.

6. The method of claim 4, further comprising heating the cylindrical bone implant or the hollow tube bone implant at between 30° to 70° Celsius for 1 minute up to 180 minutes.

7. The method of claim 6, further comprising filling the hollow tube bone implant with synthetic bone graft substitute, allograft bone chips, xenograft bone chips, and/or demineralized bone matrix (DBM), wherein the filling occurs after heating.

8. The method of claim 1, wherein the bonding of the first sheet of DBF with the second sheet of DBF to form a bone implant bag comprises annealing together three of four sides of the first sheet and the second sheet forming a cavity therebetween.

9. The method of claim 1, wherein the bone implant bag has a length from about 5 cm to about 11 cm and a width from about 5 cm to about 11 cm.

10. A method of making a bone implant bag from a sheet of demineralized bone fibers (DBF) comprising:
   providing the DBF into a sheet mold to form a sheet of DBF; and
   bonding a first sheet of DBF with a second sheet DBF to form a bone implant bag.

\* \* \* \* \*